US009457161B2

(12) United States Patent
Thoemmes et al.

(10) Patent No.: US 9,457,161 B2
(45) Date of Patent: Oct. 4, 2016

(54) INHALER (71) Applicant: Boehringer Ingelheim International GmbH, Ingelheim am Rhein (DE)

(72) Inventors: Ralf Thoemmes, Willich (DE); Jens Besseler, Dortmund (DE); Birgit Donker, Dortmund (DE); Jessica Frentzel-Beyme, Bochum (DE); Stephen William Eason, Diss (GB); Roger William Clarke, Histon (GB)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 15/071,494

(22) Filed: Mar. 16, 2016

(65) Prior Publication Data
US 2016/0193433 A1 Jul. 7, 2016

Related U.S. Application Data (63) Continuation-in-part of application No. 11/750,438, filed on May 18, 2007.

(30) Foreign Application Priority Data

May 18, 2006 (DE) .................. 10 2006 023 662

(51) Int. Cl.
*A61M 15/00* (2006.01)

(52) U.S. Cl.
CPC ....... *A61M 15/0025* (2014.02); *A61M 15/003* (2014.02); *A61M 15/004* (2014.02); *A61M 15/0045* (2013.01); *A61M 15/0051* (2014.02); *A61M 2202/064* (2013.01)

(58) Field of Classification Search
CPC ......... A61M 15/0025; A61M 15/004; A61M 15/0051; A61M 2202/064; A61M 15/003; A61M 15/0035; A61M 15/0045
See application file for complete search history.

(56) References Cited

U.S. PATENT DOCUMENTS

| 4,627,432 | A  | 12/1986 | Newell et al. |
| 5,327,883 | A  | 7/1994  | Williams et al. |
| 5,447,151 | A  | 9/1995  | Bruna et al. |
| 5,533,502 | A  | 7/1996  | Piper |
| 5,873,360 | A  | 2/1999  | Davies et al. |
| 6,971,383 | B2 | 12/2005 | Hickey et al. |
| 7,171,965 | B2 | 2/2007  | Young et al. |

(Continued)

FOREIGN PATENT DOCUMENTS

| GB | 2 242 134 A    | 9/1991 |
| JP | 2005-506163 A  | 3/2005 |
| WO | 01/26720 A1    | 4/2001 |
| WO | 03/061743 A1   | 7/2003 |
| WO | 2005/037353 A1 | 4/2005 |
| WO | 2005/049121 A1 | 6/2005 |
| WO | 2006/079746 A1 | 8/2006 |

*Primary Examiner* — Justine Yu
*Assistant Examiner* — Timothy Stanis
(74) *Attorney, Agent, or Firm* — David S. Safran (57) ABSTRACT An inhaler for delivering a preferably powdered formulation from a blister strip having a plurality of blister pouches. In order to achieve a compact simple construction for the inhaler and an easy action for the blister strip, the carrier extends over a circumferential angle of the inhaler of less than 360°. In particular, the carrier is guided between two deflectors with an at least substantially constant curvature, and preferably, exclusively along an outer wall of the inhaler. A conveying device of the inhaler has four drive wheels of the same diameter which are arranged on a common radius and are driven by common drive means in the same direction of rotation.

14 Claims, 7 Drawing Sheets

(56) References Cited

U.S. PATENT DOCUMENTS

| | | |
|---|---|---|
| 2003/0183229 A1 | 10/2003 | Smith et al. |
| 2004/0035420 A1 | 2/2004 | Davies et al. |
| 2004/0094152 A1 | 5/2004 | Harvey et al. |
| 2005/0126568 A1 | 6/2005 | Davies et al. |
| 2005/0258182 A1 | 11/2005 | Anderson |
| 2006/0196504 A1 | 9/2006 | Augustyn et al. |
| 2007/0137645 A1 | 6/2007 | Eason et al. |
| 2007/0181123 A1 | 8/2007 | Houzego |

INHALER

CROSS REFERENCE TO RELATED APPLICATION

This application is a continuation-in-part of commonly owned, co-pending U.S. patent application Ser. No. 11/750,438, filed May 18, 2007.

BACKGROUND OF THE INVENTION

1. Field of the Invention

The present invention relates to an inhaler for delivering a preferably powdered formulation from a carrier which is preferably band-shaped, flexible and/or forming a closed loop, with a plurality of receptacles.

2. Description of Related Art

The present invention relates to the delivery and atomization of a formulation particularly for inhalation or for other medical or therapeutic purposes. Particularly preferably, the present invention relates to the delivery of medical, pharmaceutical and/or therapeutic formulations which, in particular, contain or consist of at least one active substance. During atomization, an aerosol or a spray cloud is produced having, particularly for inhalation, very fine, solid and/or liquid particles, preferably in the range from 1 to 10 µm.

The formulation is preferably a powder. Particularly preferably, the invention therefore relates to a powder inhaler. The term "formulation" according to the invention preferably also includes liquids, however, while the term "liquid" is to be understood in the broad sense as including inter alia solutions, suspension, suslutions (mixture of solution and suspension), dispersions, mixtures thereof or the like.

The present invention relates to an inhaler or other atomizer for delivering a preferably powdered formulation from a reservoir such as a blister strip or other preferably disc-shaped or band-shaped carrier, having a plurality of receptacles or blister pouches, each of which contains one dose of the formulation. Therefore, the term "inhaler" is preferably to be understood generally as including other atomizers or dispensers for delivering a pre-metered formulation.

German Patent Application DE 41 06 379 A1 discloses an inhaler having a coiled blister strip. Blister pouches of the blister strip are each filled with a dose of a powdered medicament and are opened one after another for inhalation by peeling or pulling off a cover.

SUMMARY OF THE INVENTION

A primary object of the present invention is to provide an improved inhaler which while being simple in construction accommodates a preferably endless band-shaped carrier or blister strip which is optimum, particularly in terms of its compactness and/or ease of operation, and methods of delivering a preferably powdered formulation, in particular, permitting simple and/or reliable operation and/or delivery while using a simple, inexpensive construction.

The above object is achieved by means of an inhaler as described below.

According to a first aspect of the present invention it is envisaged that the carrier extends over a circumferential angle of the inhaler of less than 360°, is guided between two deflectors each of substantially constant curvature, extends solely in an annular segment of the inhaler and/or extends with one of two portions connecting the deflectors exclusively along a circumferential or outer wall of the inhaler.

These measures enable the carrier to extend as a simple loop which has the minimum possible curvature and is accordingly relatively easy to move or convey. This results in a simple but nevertheless compact construction.

Particularly preferably, the carrier is constructed as a band and/or blister strip. The receptacles are preferably formed by blister pouches. This allows simple and inexpensive manufacture.

According to a second aspect of the present invention which can also be implemented independently, the inhaler has a planet gear and/or a conveyor device having a plurality of wheels, particularly planet wheels, for stepwise advancing and/or deflecting of the carrier. The wheels are of the same diameter, are arranged on a common radius, can be driven directly or indirectly by common drive means, particularly a sun wheel or the like, and/or have the same direction of rotation. This contributes to the desired easy action of the carrier while retaining a simple and compact construction for the inhaler.

According to another aspect of the present invention which can also be implemented independently, the inhaler 1 has a conveyor device with a gear, wherein free mobility is provided in one direction of rotation. Particularly preferably, the free rotation is integrated in the sun wheel of a planet gear. This allows a simple compact construction.

According to another aspect of the present invention which can also be implemented independently, the carrier or blister strip is movable transversely of the direction of advance in order to be able to bring the receptacles containing a dose of the formulation individually up to a preferably fixed removal device and/or open said receptacles. This allows a compact simple construction and/or optimum arrangement of the removal device in the region of a mouthpiece preferably provided in the inhaler.

In another aspect of the present invention, the preferably substantially round housing of the inhaler is flattened or indented on one side, the side being formed in particular by a housing section and a section of an openable mouthpiece cover. This allows simple, intuitive operation.

In another aspect of the present invention, the carrier is moved counter to the direction of conveying, towards a travel limiter formed, in particular, by a non-return device, for the purpose of accurately positioning its receptacles or blister pouches. Thus, very precise positioning can be achieved in a very simple manner. In particular, the travel limiter is formed by a non-return device of a gear that moves the carrier along. However, the non-return device may theoretically also act directly on the carrier or blister strip.

According to another aspect of the present invention, during opening of a cover of a mouthpiece of the inhaler, only the carrier or the respective receptacle for dispensing the next dose is opened and the carrier is only moved on when the cover is closed. In this way, malfunctions particularly when only partly opening the cover are at least substantially ruled out in a simple manner.

Further aspects, features, properties and advantages of the present invention will become apparent from the following description of preferred embodiments with reference to the accompanying drawings.

DETAILED DESCRIPTION OF THE INVENTION

In the figures, the same reference numerals have been used for identical or similar parts and components; in particular, similar or corresponding advantages and/or properties are obtained even if the associated description is not repeated.

Figure 1:
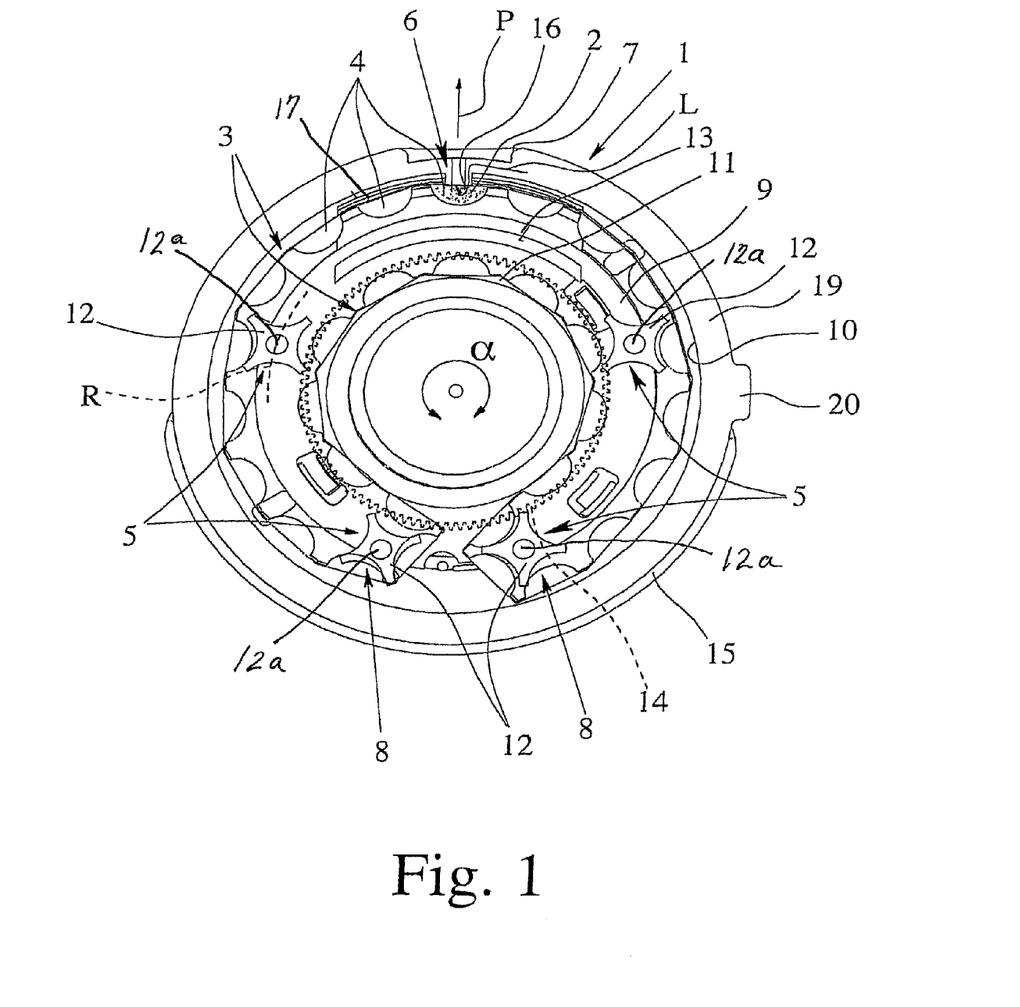
FIG. 1 is a schematic view of an inhaler according to a first embodiment in the open state.

FIG. 1 is a highly schematic representation of an inhaler 1 according to a first embodiment, in a cut-away or open state without a lid or cover.

The inhaler 1 serves to deliver a preferably powdered formulation 2 in the sense described hereinbefore from a preferably strip-shaped carrier, particularly a blister strip 3, having a plurality of receptacles, especially blister pouches 4, each of which directly contains a dose of the, in particular, loose formulation 2. The carrier forms, in particular, a closed loop, i.e., it is of circular or endless construction. For inhalation and particularly during inhalation, preferably one dose of the formulation 2 is taken from a receptacle or blister pouch 4.

The inhaler 1 has a conveyor device 5 for advancing or conveying the carrier stepwise.

The inhaler 1 also has a removing device 6 for individually opening the receptacles and/or removing the doses of formulation 2. In particular, the removal device 6 is constructed so that the receptacles can be opened individually and successively from the outside and/or by breathing in while inhaling an air current L of ambient air can be sucked in, in order to deliver the respective dose with the ambient air through an associated mouthpiece 7 of the inhaler 1, as indicated by the arrow P in FIG. 1.

The mouthpiece 7 of the inhaler 1 is preferably of rigid construction and/or is formed on or formed by a housing of the inhaler 1.

Instead of the mouthpiece 7, the inhaler 1 may also have another end-piece, for example, for nasal or other routes for administration of the formulation 2. In particular, the inhaler 1 may also be used as a nebuliser for other purposes, e.g., for the eyes. The term "inhaler" should therefore, preferably, be understood in a correspondingly general sense.

The conveying device 5 preferably has two deflectors 8 for the carrier. In particular, the carrier extends only between the deflectors 8, particularly preferably, in such a manner that the maximum possible length of carrier can be accommodated in the inhaler 1 while subjecting the carrier to the least possible and/or most uniform possible curvature, and/or so as to achieve easy action with a simple and compact construction of the inhaler 1. These individual aspects are discussed in more detail hereinafter.

The carrier is preferably guided exclusively in an annular segment 9 of the inhaler 1, as shown in FIG. 1. In particular, the inhaler 1 or the annular segment 9 forms a channel for the carrier between, in particular, a peripheral outer wall 10 and an intermediate or inner wall 11 of the inhaler 1.

The outer wall 10 extends substantially along a circle in the particularly preferred, substantially disc-shaped construction of the inhaler 1. The inner wall 11 is preferably in the form of an outer surface of a cylinder. However, other shapes are also possible.

The deflectors 8 are preferably arranged relatively close together. The carrier preferably extends away from the deflectors 8 in opposite directions.

The carrier preferably extends over a circumferential angle α of the inhaler 1 of at least 270° and/or less than 360°. Thus, a spiral or helical configuration and a resulting difficult action of the carrier can be avoided.

The carrier is guided between the two deflectors 8 with an at least substantially constant curvature. This contributes, in particular, to the desired easy action for moving or conveying the carrier.

Portions of the carrier extend between the two deflectors 8. One of these portions—in the embodiment shown, the radially outer portion—preferably extends exclusively along the outer wall 10. This makes optimum use of the space available while, in particular, achieving an at least substantially constant and/or minimal curvature of the carrier along this portion.

The deflectors 8 deflect the carrier through at least 160°, particularly at least substantially 180°. This contributes to the desired compact structure of the inhaler 1.

The portions of the carrier between the two deflectors 8 are preferably guided at an at least substantially constant spacing from one another. In particular, the radial width of the annual segment 9 or the radial spacing of the outer wall 10 from the inner wall 11 over the preferably arcuate extent of the carrier or the circumferential angle α is constant.

Preferably, the carrier runs exclusively between the two deflectors 8. In particular, the portions between the two deflectors 8 are guided at least substantially along an outer and inner arc, particularly an arc of a circle, as can be seen from FIG. 1.

In particular, the carrier is guided on the inside by means of the preferably circular or cylindrical inner wall 11. On the outside or along the outer wall 10, the carrier is preferably guided by means of the deflectors 8, wheels 12 and/or a guide element 13.

The wheels 12 are preferably all of uniform construction but may, if necessary, also be of different construction.

At least one wheel 12 is preferably constructed so that the carrier can be conveyed or moved along by interlocking engagement, so that the carrier can be advanced or conveyed onwards step by step to the next receptacle by corresponding stepwise rotation of the wheel 12. This enables the formulation 2 to be removed from the individual receptacles one after another and individually taken for delivery through the removal device 6. Preferably, all of the wheels 12 are constructed for movement or conveying of the carrier by interlocking engagement.

Particularly preferably, the wheels 12 are constructed accordingly as drive wheels or gears or pinions. Thus, in particular, the receptacles can engage in corresponding recesses in the wheels 12. Alternatively or additionally, the wheels 12 may also engage with teeth, projections or the like into corresponding recesses, openings, interstices or the like in the carrier in order to allow the desired conveying of the carrier by interlocking engagement or in defined manner.

Alternatively or additionally, the wheels 12 or at least some of the wheels 12 may also be formed as rollers or the like and/or may not enter into interlocking engagement with the carrier. Rather, the carrier may if necessary be guided only by frictional engagement or possibly by slipping or sliding. The wheels 12 are then constructed as loose, non-driven rollers or the like.

Theoretically, the deflectors 8 or wheels 12 may also be formed by sliding elements or other guide means. However, it is particularly preferred that the deflectors 8 should be formed by wheels 12.

In the embodiment shown, two wheels 12 form the deflectors 8. In addition, at least two other wheels 12 are preferably provided for guiding the carrier, particularly, the outer portion of the carrier, on or along the outer wall 10. However, these additional wheels 12 may also be omitted entirely. In this case, in particular, corresponding guides, channels or wall portions are provided for adequately guiding the portions of the carrier between the deflectors 8.

The two deflectors 8 are preferably arranged on the side of the inhaler 1 opposite the removal device 6 or mouthpiece 7. Particularly preferably, the carrier is arranged symmetrically with respect to the removal device 6 and/or mouthpiece 7. Alternatively or additionally, this is preferably also true of the arrangement of the wheels 12.

A particular advantage of the proposed guiding of the carrier in the inhaler 1 is that the carrier is only relatively highly curved in the region of the deflectors 8, and in particular, is only curved in the same direction. In particular, there is no sharp curve in the opposite direction. This contributes to the desired easy action during the conveying or movement of the carrier.

The wheels 12 preferably have the same diameter and are identical in construction. This makes manufacture simple and inexpensive. Particularly preferably, the diameter of the wheels 12 substantially corresponds to the spacing of the portions of the carrier.

The wheels 12 are preferably arranged on a line having a constant radius R (dash line in FIG. 1). In particular, this permits simple driving. Preferably, in fact, the wheels 12 can be driven by a common drive means, especially a sun wheel 14, which is only partly shown in FIG. 1. In this case a kind of planet gear is formed with the wheels 12. Preferably, the wheels 12 have teeth in the manner of a gear, to allow a defined movement or conveying of the carrier. Alternatively, the wheels 12 may also be driveable, for example, by means of an encircling belt or the like as a common drive means.

Particularly preferably, the wheels 12 rotate in the same direction in order to move or convey the carrier.

Thus, during the actuation of the conveying device 5, the carrier continues to be advanced or conveyed onwards in a rotary manner, and indeed is advanced stepwise to the next receptacle for the next delivery or inhalation.

The conveying device 5 preferably forms the only drive for moving the carrier.

The mouthpiece 7 or other endpiece preferably has an associated cover 15 which is movable, in particular pivotable, in order to open and/or close the mouthpiece 7. The conveying device 5 and/or removal device 6 is preferably actuated by the opening and/or closing movement of the cover 15. This provides a very simple, and in particular, intuitive method of actuating and using the inhaler 1.

The removal device 6 preferably has a removal element 16 which is constructed, in particular, as a piercing element, is of fixed design and/or attached to the mouthpiece 7. The removal element 16 is movable relative to the respective receptacle or relative to the carrier in order to open the respective receptacle, in particular to pierce it, and thereby establish a fluidic connection with the receptacle in question.

Preferably, the relative movement is carried out by the carrier being moved by the guide element 13 or in some other way, in particular, pushed transversely with respect to its direction of movement or conveying. For this purpose the guide element 13 is correspondingly guided to be movable, particularly slideable, most preferably in the manner of a sled. This direction of movement or sliding is, in particular, in the radial direction, in the embodiment shown, or counter to the direction of delivery or the arrow P.

Figure 2:
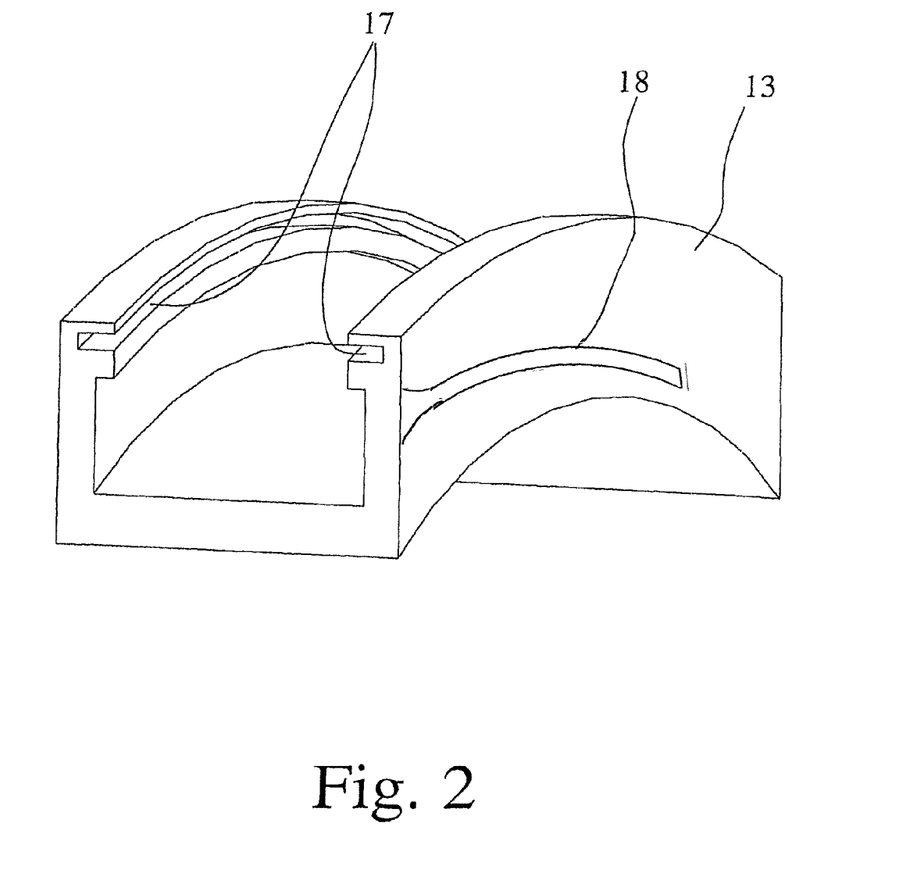
FIG. 2 is a perspective view of a guide portion of the inhaler.

FIG. 2 is a perspective view of a preferred construction of the guide element 13. The guide element 13 guides the carrier preferably by interlocking engagement, e.g., in opposing longitudinal grooves 17 which open towards one another. However, other constructional solutions are also possible.

Figure 3:
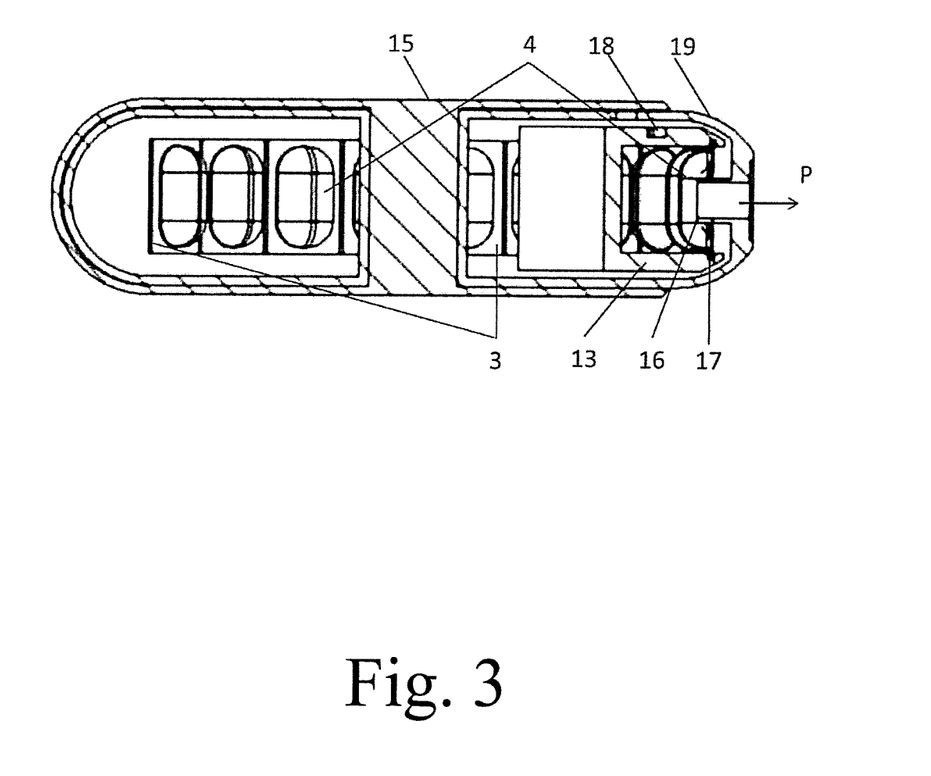
FIG. 3 is a sectional view through a part of the inhaler in the region of a mouthpiece.
Figure 3A:
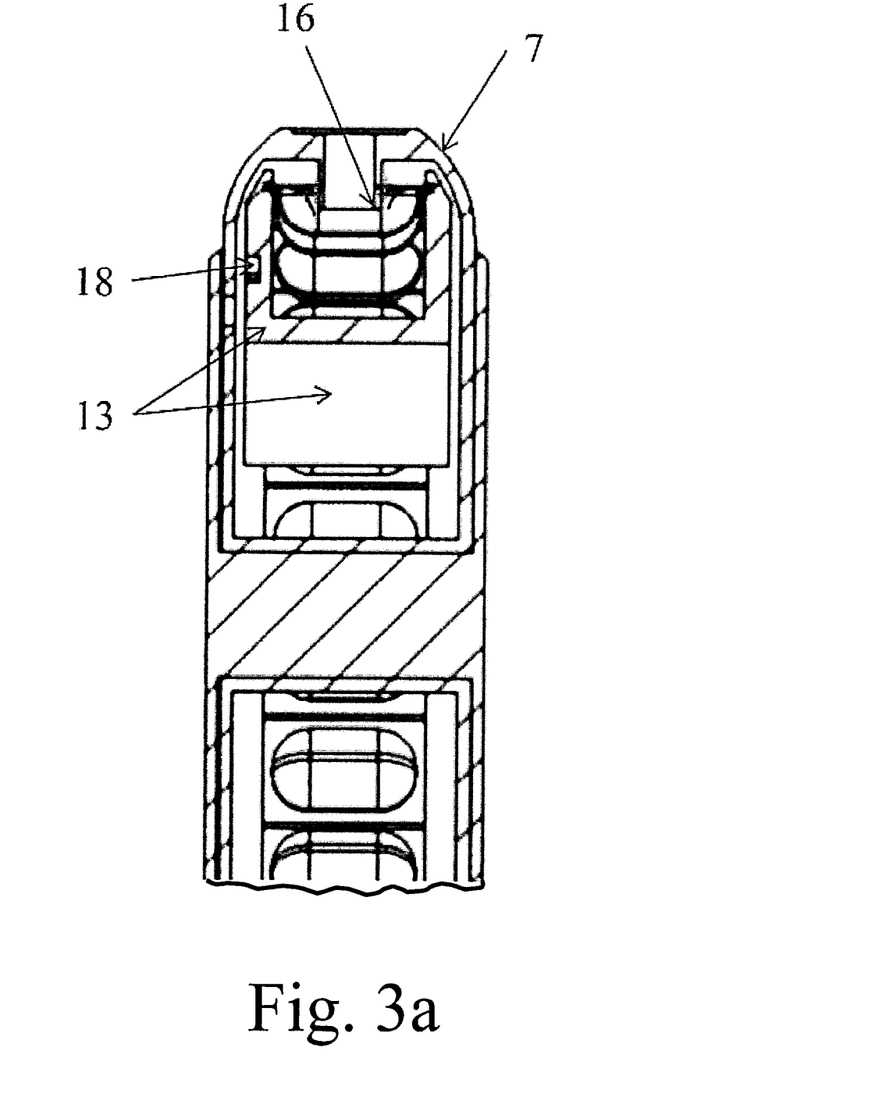
FIG. 3a is an enlarged view of the portion of FIG. 3 in the area of the mouthpiece.
Figure 3B:
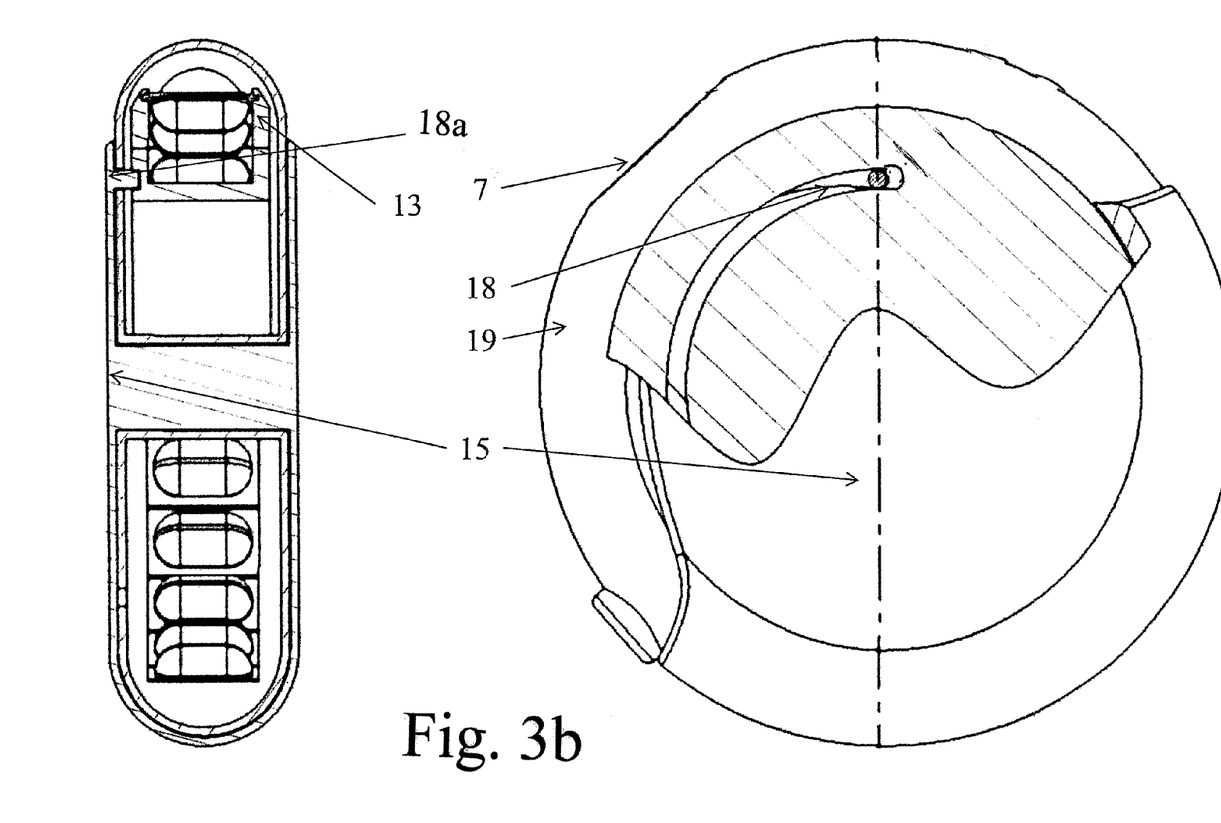
FIG. 3b shows an example of a cam pin on the cover engaged in the control curve of the guide element, the left hand view being vertical cross section along the dot-dash line of the partially broken away side view on the right in the figure.

Moreover, FIG. 2 shows a preferably exterior sliding surface, control groove or control curve 18 on the guide element 13. The control curve (curved slot) 18 in the guide element 13 is a cam slot that is to be moved by a cam pin provided on the cover, and due to the downward trajectory of the cam slot, the guide element 13 would be raised as the cam pin moves in the slot. The cam pin on the cover 15 can engage directly in the control curve 18, so that the guide element 13, and with it the carrier, are moved or displaced in the desired manner relative to the removal element 16 for selectively opening or making contact with the respective receptacle. In particular, a sliding or forcible guide is formed for moving the guide element 13 or the carrier in a defined manner as desired. That is, control curve 18 is engaged and disengaged by a control element on the inner side of the cover 15 for which purpose the control curve can be provided with widened mouth with curved surfaces to assist movement of the cam pin into the control curve. FIG. 3b more clearly shows an example of a cam pin 18a on the cover 15 engaged in the control curve 18. Due to the curvature of the control curve 18, the guide element 13 is pulled up as the cover is opened and is pushed down as the cover is closed. However, other geared solutions or actuations are also possible.

For use, the cover 15 of the inhaler 1 is opened, for example, by pivoting or rotating about a central axis of the inhaler 1. This exposes the mouthpiece 7. Before this, at the same time or subsequently, the conveying device 5 is actuated or the carrier is advanced to the next receptacle and/or the next receptacle is opened. This is achieved, in particular, by means of a suitable geared coupling of the cover 15 with the conveying device 5, particularly preferably, with the sun wheel 14.

After the carrier has been advanced in the desired manner, and preferably as the opening or pivoting movement of the cover 15 continues, the receptacle intended for the next inhalation, and in particular, already positioned relative to or underneath the removal element 16, is opened. To open it, the guide element 13 or the carrier is moved relative to the removal element 16 such that the latter opens the receptacle, particularly engages in a foil cover or covering of the blister pouch 3 and cuts it open, pierces it or tears it open. This state is illustrated in FIG. 1 and in FIG. 3. In this state, the cover 15 is fully open and the inhaler 1 is ready for delivery or inhalation.

According to a particularly preferred alternative feature, the carrier is not conveyed further during the opening of the cover 15, but is opened only in the course of the opening movement (in particular, only at the end of the opening movement). In particular, the respective receptacle of the carrier is pierced by the removal element 16. Particularly preferably, the opening is carried out by moving the carrier or the corresponding receptacle up to the preferably stationary removal element 16. In this way, the opening movement is at an end and the cover 15 is fully open. Now, the delivery or inhalation of the dose contained in the open receptacle can take place.

Once the delivery or inhalation of the dose has ended, the cover 15 is closed again. During the closing movement, first of all, in a first phase, the removal element 16 and the carrier are moved away from one another, and in particular, the carrier is moved away from the removal element 16 again, so that the carrier can be moved onwards. Then, in a second phase of the closing movement of the cover 15, the carrier is moved on, so that the next receptacle is already in position or at least substantially correctly positioned. This procedure has the advantage that partial opening of the inhaler 1 or cover 15, starting from the closed position, does not lead to any further movement of the carrier.

In the alternative feature described above, a freewheeling clutch 22 or a non-return device 28 ensures, as explained hereinafter with reference to a second embodiment, that the carrier does not move back during the opening of the cover 15 or is only moved back slightly for accurate positioning.

Figure 4:
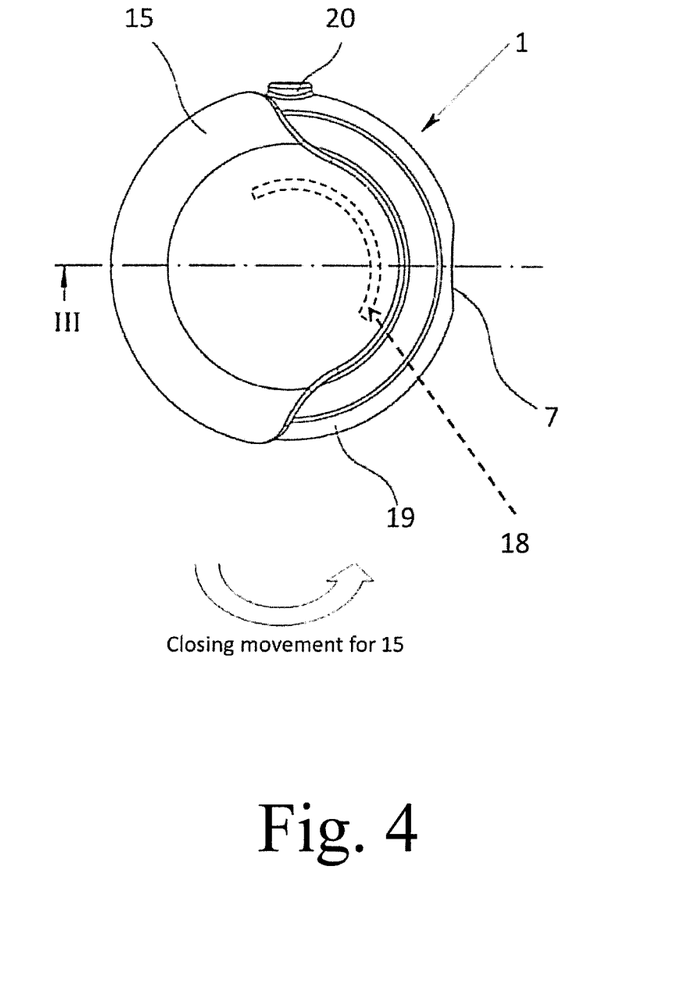
FIG. 4 is an external view of the inhaler.

FIG. 4 shows the inhaler 1 in exterior view with the cover 15 open. The cover 15 surrounds the preferably disk-shaped housing 19 of the inhaler 1 which is, in particular, in the shape of a sector on both sides and along a circumferential angle or circumferential portion of, for example, about 120 to 180°. Preferably, at least one stop, in this case, a radial stop 20, is provided for limiting the pivoting movement, in particular, both the opening movement and the closing movement.

When a user or patient breathes or sucks in air through the mouthpiece 7, the current L of ambient air (FIG. 1) is sucked in and conducted through the opened or pierced receptacle in such a way that the formulation 2 contained in the receptacle is delivered by the air current L through the removal element 16 and the adjoining mouthpiece 7 in nebulised form, i.e., as an aerosol cloud or spray mist.

After the receptacle has been emptied and the formulation 2 delivered, the inhaler 1 or the cover 15 can be closed again. To do this, the cover 15 is preferably rotated or pivoted counter to the direction of opening. A corresponding freedom of movement or locking mechanism ensures that the carrier or blister strip 3 is not moved or conveyed in the opposite direction in undesirable manner.

According to the alternative version, in addition to or in particular as an alternative to the opening movement, the closing movement may also be used to actuate the conveying device 5 or to advance or further convey the carrier on to the next receptacle.

The inhaler 1 is preferably portable in construction. Particularly preferably, it operates purely mechanically.

The inhaler 1 preferably comprises a counter (not shown) for counting and displaying the receptacles which have already been used or those which have not yet been used.

A second embodiment of the proposed inhaler 1 will now be described in more detail with reference to FIG. 5. Only major differences from the first embodiment will be described here, in particular, which means that the other remarks and explanations still apply accordingly or in supplementary manner.

Figure 5:
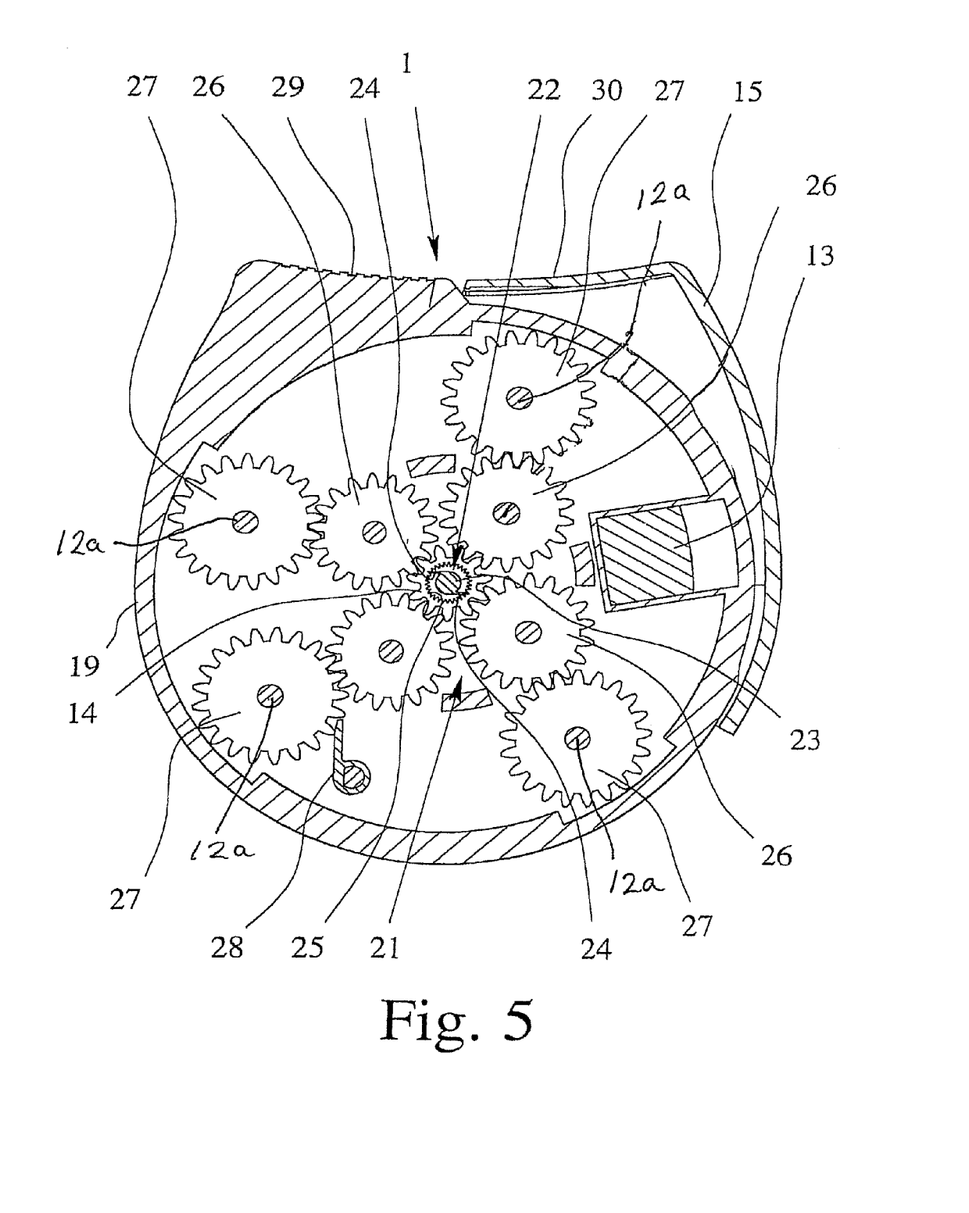
FIG. 5 is a schematic view of an inhaler according to a second embodiment in the open position and in schematic section.

In the second embodiment, in the section according to FIG. 5, a gear is shown, particularly a gearwheel or planetary gear 21, of the inhaler 1 or of the conveying device 5 for advancing or further conveying the carrier. However, theoretically, any other suitable gear may be used, although the planet gear 21 is particularly preferred.

Preferably, the inhaler 1 or the conveying device 5 comprises a ratchet pinion 22 that is free running in a direction of driving or rotation of the drive train or gear.

Particularly preferably, the free wheel clutch 22 is associated with a drive wheel or gearwheel, particularly the sun wheel 14, or is arranged or integrated therein. In the embodiment shown, the free wheel clutch 22 comprises a drive element 23 with at least one preferably tangentially and/or radially projecting finger 24 (most preferably two fingers 24). The drive element 23 makes interlocking engagement by means of the finger 24 or fingers 24 on the associated drive or gearwheel or sun wheel 14 in order to drive the latter in this direction. In the other direction or rotation the fingers 24 can glide or slip through. In particular, inner teeth 25 are formed on the associated drive or gearwheel or sun wheel 14 on which the fingers 24 can engage. However, other constructional solutions are also possible.

The sun wheel 14 preferably drives associated planet wheels 27 of the planet gear 21 via intermediate gears 26. The intermediate gears 26 are preferably uniformly distributed about the sun wheel 14 in order to achieve a particularly compact structure. Alternatively, the sun wheel 14 may also drive the planet wheels 27 directly.

The planet wheels 27 are preferably arranged coaxially with the wheels 12 for guiding and/or conveying the carrier. Particularly preferably, the planet wheels 27 are mounted about wheels 12, in pairs on a common axle 12a and/or are of integral construction. For example, the planet wheels 27 may be formed on the wheels 12 or vice versa.

The inhaler 1 or the conveying device 5, preferably, has a non-return mechanism 28 to safely prevent undesirable reversing of the carrier and/or to form a defined end stop to the movement of the carrier. The non-return mechanism 28 preferably works on the conveying device 5 or its gear, i.e., in the embodiment shown on a planet wheel 27. For example, the non-return mechanism 28 may be formed by an, in particular, elastically biased locking latch or the like which prevents the unwanted backwards rotation and reversing. Alternatively or additionally, the non-return mechanism 28 may also act on the carrier itself.

In the embodiment shown the drive element 23 is preferably coupled in a driving relationship with the cover 15, so that the drive element 23 is rotated at the same time during opening and closing. In one direction of rotation the free wheel clutch 22 locks in place and rotates the sun wheel 14 in order to drive the planet wheels 27 and according convey the carrier onwards by means of the wheels 12. In the other direction of rotation the free wheel clutch 22 comes into effect or rotates or slips through, at least under the effect of the non-return mechanism 28, so that the carrier is no longer moved backwards or at most is moved as far as the stop or the barrier of the non-return mechanism 28. This reversing as far as a defined stop by means of the non-return mechanism 28 can be achieved by corresponding frictional or forceful engagement of the free wheel clutch 22 in the reverse direction and/or it can be used for highly accurate positioning of the carrier.

Preferably, the inhaler 1 is constructed such that the carrier is initially always advanced somewhat too far as it moves on to the next receptacle. Before the receptacle is opened, the carrier is then moved back to the travel limiter or until the non-return mechanism 28 comes into effect. Thus, the receptacle which is to be opened is initially positioned very precisely in the removal position in which opening takes place, particularly by moving it up to the removal element 16.

Particularly preferably, the reversing of the carrier or of the receptacle in the carrier which is to be opened, up to a defined end stop (formed by the non-return mechanism 28), is used in the alternative embodiment already described above (advancing of the carrier only when the cover 15 is shut) so that during the initial opening of the inhaler 1 or of the cover 15 the carrier is moved back to the stop and the receptacle which is to be opened is accurately positioned relative to the removal element 16. The actual opening of the receptacle then takes place in the course of the further opening movement of the cover 15, as already explained.

Generally speaking, it is pointed out that the free wheel clutch 22 may also be produced in some other way. The non-return mechanism 28 can also be formed in some other way. In particular, the non-return mechanism 28 may, if necessary, also act directly on the carrier 2, optionally even directly on the receptacles or blister pouches 4.

It should be noted that the opened covered 15, in turn, preferably exposes the mouthpiece 7, although this is not shown in FIG. 5.

FIG. 5 shows the preferred sled-like guiding of the guide element 13, preferably by means of the housing of the inhaler 1, in purely schematic form.

The inhaler 1 or its housing 19 has, in particular, a substantially round shape and/or a flattened or indented (concave) side. In the embodiment shown by way of example, this flattened or indented side is particularly preferably formed by a portion 29 of the housing 19 of the inhaler 1 and/or by a portion 30 of the cover 15. The portion 29 serves, in particular, for holding or gripping the inhaler 1 or as an abutment surface for a finger, especially a thumb, of the user. The portion 30 serves, in particular, as an actuating surface, preferably for a finger or thumb of the user, during opening or for the purpose of opening the cover 15. When the inhaler 1 is closed, the portions 29, 30 are preferably located side by side and form, in particular, an at least substantially continuous outer surface of the inhaler 1. To open the cover 15, the portions 29, 30 can be pushed apart. This allows very simple and/or intuitive operation.

Generally, it is pointed out regarding the two embodiments that the carrier 3 is preferably moved or displaced at right angles or perpendicular to the direction of conveying or in the radial direction, in order to fluidically connect the respective receptacle or blister pouch 4 to the removal device 6 or the removal element 16 thereof, and/or to open said receptacle or pouch 4. The removal device 6 or its removal element 16 is correspondingly preferably fixed in construction. After the removal or inhalation of the formulation 2 from the respective blister pouch 4, the carrier is preferably moved back again in the opposite direction to allow the carrier to be conveyed onwards.

The lateral movement of the carrier for the purpose of opening it is preferably carried out by the opening or closing movement of the cover 15, particularly separately from the gear, particularly preferably by means of a sliding guide or other forced guide, which correspondingly moves or displaces the guide element 13 and hence the carrier or the receptacle located in the removal position, with the desired dependency on the movement of the cover 15 (in this case towards or away from the removal element 16)

Individual features and aspects of the two embodiments may also be combined with one another as desired and/or used in other inhalers 1.

What is claimed is:

1. An inhaler for delivering a powdered formulation from a flexible strip with a plurality of individual receptacles, each of which contains a dose of the formulation, comprising:
   a removal device having a piercing element adapted for opening the receptacles individually for removal of the doses of formulation,
   a conveying device for advancing the strip stepwise so as to bring an individual receptacle to be opened into alignment with the piercing element,
   a cam and follower arrangement for moving at least a portion of the strip with an individual receptacle to be opened to the piercing element so as to cause the individual receptacle to be opened by the piercing element after the strip has been advanced by the conveying device; and
   a mouthpiece for delivering the formulation in nebulized or atomized form and an associated cover which is movable for opening and closing the mouthpiece, and
   wherein the conveying device is actuated by at least one of the opening and dosing movements of the cover.

2. The inhaler according to claim 1, wherein the cam and follower arrangement comprises a guide element which is movable in a sliding manner relative to the piercing element, a slot being formed in the guide element that is engaged by a pin displaced along the slot by movement of the cover.

3. The inhaler according to claim 1, wherein the conveying device; for stepwise advancing of the strip; comprises deflectors between which the strip extends, the conveying device being operable to advance the flexible strip around said deflectors, and at least one of the following features: the strip extends over a circumferential angle of the inhaler of less than 3600;
   the strip is guided between the deflectors with an at least substantially constant curvature;
   the strip extends exclusively in an annular segment of the inhaler; and
   a portion of the strip between the deflectors extends exclusively along an outer wall of the inhaler.

4. The inhaler according to claim 3, wherein the strip extends exclusively between two deflectors.

5. The inhaler according to claim 3, wherein the strip is guided between two deflectors, at least substantially along an outer and inner arc.

6. The inhaler according to claim 3, wherein each of the deflectors deflect the strip through at least 1600.

7. The inhaler according to claim 3, wherein portions of the strip between the deflectors are guided at an at least substantially constant spacing from one another.

8. The inhaler according to claim 3, wherein the conveying device has a non-return mechanism which forms a travel limiter for preventing reverse movement of the strip to position the respective receptacle in a defined position for a next delivery.

9. The inhaler according to claim 1, wherein the conveying device comprises a plurality of wheels for at least one of stepwise advancing and guiding of the strip;
   wherein the wheels are of equal diameter, are at the same radial distance from the center of the inhaler, are driven by common drive means, and have the same direction of rotation.

10. The inhaler according to claim 9, wherein the wheels have a diameter that essentially corresponds to the spacing of the receptacles.

11. The inhaler according to claim 9, wherein said plurality of wheels of the conveying device directly act on the strip and all of the wheels acting on the strip are driven.

12. The inhaler according to claim 1, wherein the conveying device forms the sole drive for moving the strip.

13. The inhaler according to claim 1, comprising a substantially round housing which is flattened or indented on one side.

14. The inhaler according to claim 13, wherein the flattened or indented side is formed by a portion of the housing and by a portion of a cover of the inhaler which is adjacent to said portion of the housing when the inhaler is closed.

* * * * *